United States Patent
Fung et al.

(10) Patent No.: US 8,941,499 B2
(45) Date of Patent: Jan. 27, 2015

(54) MONITORING SYSTEM FOR USE WITH A VEHICLE AND METHOD OF ASSEMBLING SAME

(75) Inventors: Kin Fung, Dublin, OH (US); Timothy Dick, Dublin, OH (US)

(73) Assignee: Honda Motor Co., Ltd., Tokyo (JP)

( * ) Notice: Subject to any disclaimer, the term of this patent is extended or adjusted under 35 U.S.C. 154(b) by 380 days.

(21) Appl. No.: 13/195,675

(22) Filed: Aug. 1, 2011

(65) Prior Publication Data

US 2013/0033382 A1 Feb. 7, 2013

(51) Int. Cl.
*G08B 23/00* (2006.01)
*A61B 5/00* (2006.01)
*B60K 28/06* (2006.01)
*G08B 21/06* (2006.01)
*A61B 5/024* (2006.01)

(52) U.S. Cl.
CPC ............... *A61B 5/6893* (2013.01); *B60K 28/06* (2013.01); *G08B 21/06* (2013.01); *A61B 5/6831* (2013.01); *A61B 5/721* (2013.01); *A61B 5/024* (2013.01); *A61B 5/6823* (2013.01); *A61B 2503/22* (2013.01)
USPC ...................... 340/573.1; 340/575; 340/425.5; 340/457

(58) Field of Classification Search
CPC ....................................................... G08B 21/06
USPC ......... 340/539.12, 573.1, 501, 506, 511, 575, 340/425.5, 457, 457.1; 600/300
See application file for complete search history.

(56) References Cited

U.S. PATENT DOCUMENTS

| | | | |
|---|---|---|---|
| 5,783,997 A | 7/1998 | Saitoh et al. | |
| 6,195,008 B1 * | 2/2001 | Bader | 340/573.1 |
| 6,459,365 B2 | 10/2002 | Tamura | |
| 6,575,902 B1 * | 6/2003 | Burton | 600/300 |
| 6,603,999 B2 * | 8/2003 | SerVaas | 607/5 |
| 7,183,930 B2 | 2/2007 | Basir et al. | |
| 7,219,923 B2 | 5/2007 | Fujita et al. | |
| 7,254,439 B2 | 8/2007 | Misczynski et al. | |
| 7,482,938 B2 | 1/2009 | Suzuki | |
| 2005/0080533 A1 | 4/2005 | Basir et al. | |
| 2006/0283652 A1 | 12/2006 | Yanai et al. | |
| 2008/0071177 A1 | 3/2008 | Yanagidaira et al. | |
| 2008/0228046 A1 | 9/2008 | Futatsuyama et al. | |

(Continued)

FOREIGN PATENT DOCUMENTS

| | | | |
|---|---|---|---|
| JP | 2001260698 A | 9/2001 | |
| JP | 2002102188 A | 4/2002 | |
| JP | 2006346109 A | 12/2006 | |

(Continued)

OTHER PUBLICATIONS

PCT International Search Report of related application PCT/US2012/030260 dated Jun. 20, 2012.

*Primary Examiner* — Benjamin C Lee
*Assistant Examiner* — Rajsheed Black-Childress
(74) *Attorney, Agent, or Firm* — Rankin, Hill & Clark LLP

(57) ABSTRACT

A first sensor is coupled to a seat back surface and/or a seat belt, and a second sensor is positioned remotely from the first sensor. The first sensor is configured to generate a raw signal indicative of biological data and noise, and the second sensor is configured to generate a baseline signal indicative of noise associated with the first sensor. A computing device is programmed to determine a state of the occupant based on at least the raw signal and the baseline signal.

16 Claims, 2 Drawing Sheets

(56) References Cited

U.S. PATENT DOCUMENTS

2009/0289780 A1 11/2009 Tenorio-Fox
2009/0326399 A1 12/2009 Batalloso et al.
2010/0168527 A1 7/2010 Zumo et al.

FOREIGN PATENT DOCUMENTS

| JP | 2007244479 A | 9/2007 |
| JP | 2008229091 A | 10/2008 |
| JP | 2009142576 A | 7/2009 |

* cited by examiner

MONITORING SYSTEM FOR USE WITH A VEHICLE AND METHOD OF ASSEMBLING SAME

BACKGROUND

The present disclosure relates generally to monitoring systems and, more particularly, to methods and systems for use in monitoring a heart rate and/or a blood flow rate of an occupant of a vehicle.

At least some known vehicles include a plurality of sensors that may be used to detect a heart rate. For example, at least some known vehicles include an alarm device that provides a signal that is indicative of a driver's excitement, exhaustion, stress, and/or drowsiness. However, at least some known heart rate detections have a low signal-to-noise ratio because the heart rate signal may be relatively weak and/or because the environmental noise may be relatively high.

For example, at least one known monitoring system includes a steering wheel, a first sensor positioned at the ten o'clock position of the steering wheel, and a second sensor positioned at the two o'clock position of the steering wheel. In such a system, the heart rate signal may be relatively weak when a driver's hands are moved away from the ten and two o'clock positions. To facilitate continuously detecting the driver's heart rate, another known monitoring system includes a sensor positioned on a driver's seat. In such a system, the environmental noise may be relatively high because different clothing types and/or clothing layering may require a different tuned circuit to obtain a desired waveform. As such, the benefits and/or uses of known vehicle monitoring systems may be limited.

BRIEF DESCRIPTION

In one aspect, a monitoring system is provided for use in determining a state of an occupant of a vehicle. The monitoring system includes a seat including a seat back surface and a seat belt removably coupled to the seat. A first sensor configured to generate a raw signal indicative of biological data and noise is coupled to the seat back surface and/or the seat belt. A second sensor configured to generate a baseline signal indicative of noise associated with the first sensor is positioned remotely from the first sensor. A computing device is programmed to determine the state of the occupant based on at least the raw signal and the baseline signal.

In another aspect, a monitoring system is provided for determining a state of an occupant of a vehicle. The system includes a seat belt including a sash belt portion, a first sensor coupled to the sash belt portion, and a second sensor positioned remotely from the first sensor. The first sensor includes a piezoelectric film configured to generate a raw signal indicative of biological data and noise, and the second sensor is configured to generate a baseline signal indicative of noise associated with the first sensor. A computing device is programmed to determine the state of the occupant based on at least the raw signal and the baseline signal.

In yet another aspect, a method is provided for assembling a monitoring system that may be used to determine a state of an occupant of a vehicle. The method includes coupling a first sensor to a seat back surface and/or a seat belt. The first sensor is configured to generate a raw signal indicative of biological data and noise. A second sensor configured to generate a baseline signal indicative of noise associated with the first sensor is positioned remotely from the first sensor. The first and second sensors are coupled to a computing device programmed to determine the state of the occupant based on at least the raw signal and the baseline signal.

The features, functions, and advantages described herein may be achieved independently in various embodiments of the present disclosure or may be combined in yet other embodiments, further details of which may be seen with reference to the following description and drawings.

Although specific features of various embodiments may be shown in some drawings and not in others, this is for convenience only. Any feature of any drawing may be referenced and/or claimed in combination with any feature of any other drawing.

DETAILED DESCRIPTION

The subject matter described herein relates generally to monitoring systems and, more particularly, to methods and systems for use in measuring a heart rate and/or a blood flow rate of an occupant of a vehicle using a piezoelectric sound pressure vibration sensor. In one embodiment, the monitoring system includes a first sensor that is positioned in close proximity to the occupant's heart when the system is in use, and a second sensor that is positioned remotely from the first sensor. In such an embodiment, the first sensor generates a raw signal indicative of biological data and noise, and the second sensor generates a baseline signal indicative of the noise associated with the first sensor. Based on at least the raw signal and the baseline signal, a state of the occupant may be determined.

As used herein, an element or step recited in the singular and proceeded with the word "a" or "an" should be understood as not excluding plural elements or steps unless such exclusion is explicitly recited. Furthermore, references to "one embodiment" of the present invention or the "exemplary embodiment" are not intended to be interpreted as excluding the existence of additional embodiments that also incorporate the recited features.

Figure 1:
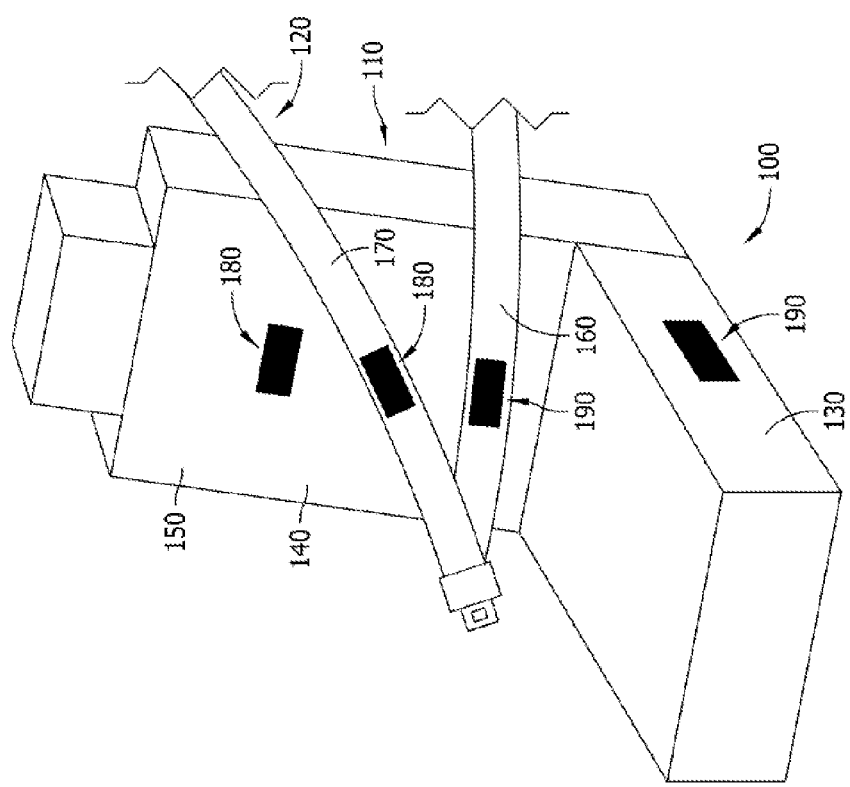
FIG. 1 is a perspective view of an exemplary vehicle seat and an associated seat belt that may be used to selectively couple an occupant to the seat.

FIG. 1 illustrates an exemplary monitoring system 100 that includes a seat 110 and a seat belt 120 that is selectively coupleable to seat 110 to secure an occupant (not shown) within seat 110. More specifically, in the exemplary embodiment, seat belt 120 is selectively moveable between an engaged configuration (shown generally in FIG. 1), wherein seat belt 120 is coupled to seat 110, and a disengaged configuration (not shown), wherein at least a portion of seat belt 120 is uncoupled from seat 110.

In the exemplary embodiment, seat 110 and/or seat belt 120 are used within a vehicle (not shown). As used herein, the term "vehicle" refers to any mechanism that conveys and/or transports an object and/or person from one location to another. For example, vehicles may include, without limitation, an automobile, a train, a boat, and/or an airplane. In the exemplary embodiment, seat belt 120 secures a driver (not shown) within seat 110 when seat belt 120 is in the engaged configuration. Moreover, the driver may freely move with respect to seat 110 when seat belt 120 is in the disengaged configuration. As described herein, monitoring system 100 is used to monitor a driver of the vehicle. Additionally or alternatively, system 100 may be configured to monitor any other occupant of the vehicle.

In the exemplary embodiment, seat 110 includes a lower support 130 and a back support 140 that extends generally upward from lower support 130. Back support 140 includes a seat back surface 150 that is oriented to face a front (not shown) of the vehicle. In the exemplary embodiment, seat belt 120 is selectively extendable across seat back surface 150. More specifically, in the exemplary embodiment, a lap belt portion 160 of seat belt 120 is extendable substantially horizontally with respect to seat back surface 150, and a sash belt portion 170 of seat belt 120 is extendable substantially diagonally with respect to seat back surface 150. Alternatively, seat belt 120 may be extendable in any direction that enables system 100 to function as described herein.

In the exemplary embodiment, when system 100 is used, a first sensor 180 is positioned to detect an occupant's heart rate and/or blood flow rate. More specifically, in the exemplary embodiment, first sensor 180 detects an occupant's heart rate and/or blood flow rate when the occupant is secured within seat 110 and seat belt 120 is in the engaged configuration. For example, in the exemplary embodiment, when seat belt 120 is in the engaged configuration, first sensor 180 is positioned in relative close proximity to the occupant's heart. More specifically, in the exemplary embodiment, first sensor 180 is coupled to seat belt 120 or, more specifically, to sash belt portion 170 and/or to seat back surface 150. Alternatively, first sensor 180 may be positioned in any other location that enables system 100 to function as described herein.

In the exemplary embodiment, first sensor 180 has a passive state, as described above, and an active state. In the exemplary embodiment, first sensor 180 generates a raw signal (not shown), when in the active state, that is representative of biological data and noise detected and/or measured by first sensor 180. More specifically, in the exemplary embodiment, the raw signal is generated proportional to a mechanical stress and/or vibration detected by first sensor 180. Moreover, in the exemplary embodiment, first sensor 180 generates an alert signal (not shown), when in the active state, that is detectable by the occupant. For example, in one embodiment, first sensor 180 is used to produce a tactile and/or audible signal that may be detected by the occupant. As used herein, the term "biological data" is used to refer to data associated with the occupant's heart rate, blood flow rate, and/or breathing rate. Moreover, as used herein, the term "noise" is used to refer to sensor detections other than biological data.

Furthermore, in the exemplary embodiment, a second sensor 190 is positioned remotely from first sensor 180. More specifically, in the exemplary embodiment, second sensor 190 is positioned to detect noise that is substantially similar to noise detected by first sensor 180. For example, in the exemplary embodiment, second sensor 190 is coupled to seat belt 120 or, more particularly, to lap belt portion 160 and/or to lower support 130. Alternatively, second sensor 190 may be positioned in any other location that enables system 100 to function as described herein.

In the exemplary embodiment, second sensor 190 generates a baseline signal (not shown) that is representative of noise and, more particularly, noise that is substantially similar to noise subjected to and detected by first sensor 180. More specifically, in the exemplary embodiment, the baseline signal generated is proportional to mechanical stresses and/or vibrations detected by second sensor 190.

In the exemplary embodiment, first sensor 180 and/or second sensor 190 is formed with a thin film (not shown) that is flexible, lightweight, and/or durable. As such, in the exemplary embodiment, the thin film may be contoured to be generally ergonomic and/or comfortable to the occupant being monitored by system 100. For example, in the exemplary embodiment, the thin film has a substantially low profile with a thickness (not shown) that is, for example, less than 600 nm. More particularly, in the exemplary embodiment, the thin film thickness is between approximately 100 nm and 300 nm. Moreover, in the exemplary embodiment, the flexibility and durability of the material used enables first sensor 180 and/or second sensor 190 to be embedded in seat 110 and/or seat belt 120. Alternatively, the thin film may have any thickness that enables first sensor 180 and/or second sensor 190 to function as described herein. In the exemplary embodiment, the thin film is fabricated from a thermoplastic fluropolymer, such as polyvinylidene fluoride, and poled in an electric field to induce a net dipole moment on sensor 180 and/or 190. Alternatively, the thin film may be fabricated from any material that enables first sensor 180 and/or second sensor 190 to function as described herein.

Figure 2:
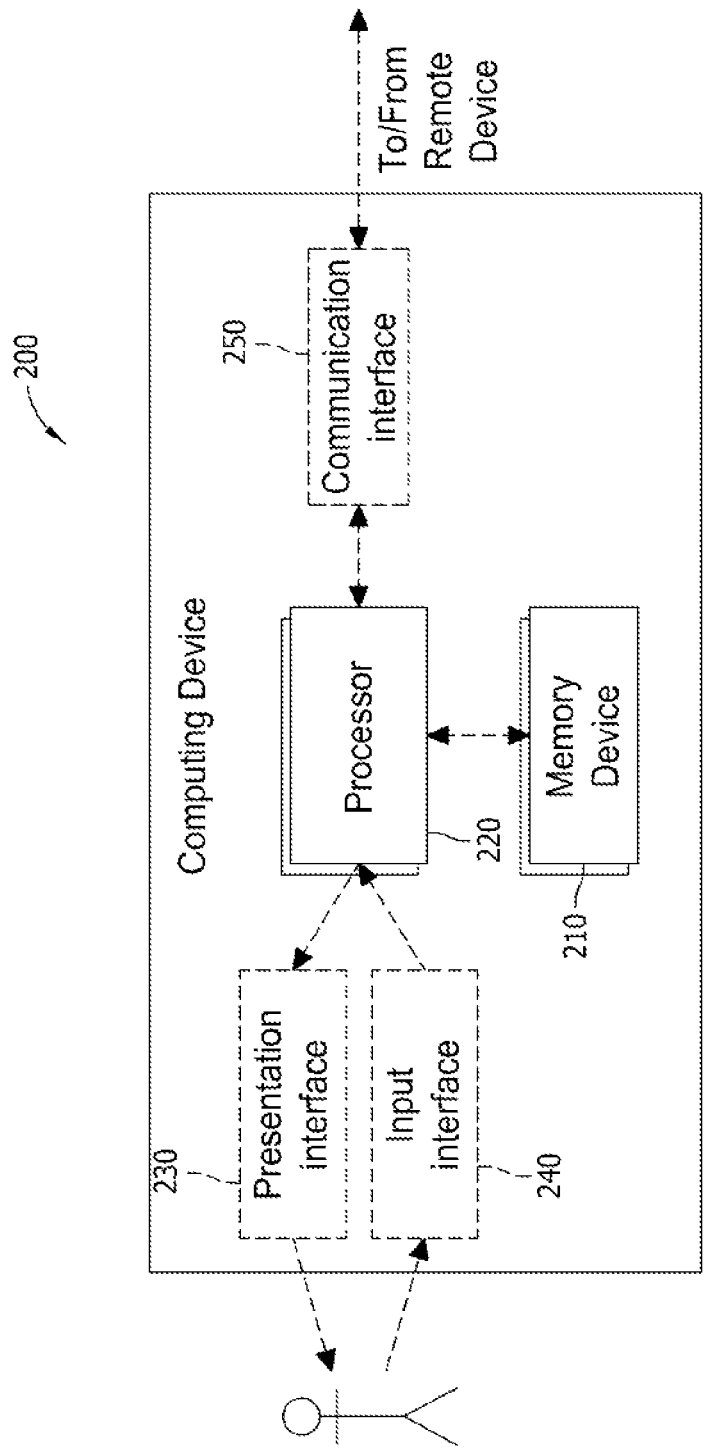
FIG. 2 is a block diagram of an exemplary computing device that may be used with the seat and seat belt shown in FIG. 1.

FIG. 2 is a block diagram of an exemplary computing device 200 that maybe used with monitoring system 100. In the exemplary embodiment, computing device 200 determines a state of the occupant based on raw signals generated by first sensor 180 and/or baseline signals generated by second sensor 190. More specifically, in the exemplary embodiment, computing device 200 receives the raw signal from first sensor 180 and the baseline signal from second sensor 190, and generates a desired signal (not shown) after determining a difference between the raw signal and the baseline signal. That is, in the exemplary embodiment, computing device 200 increases a signal-to-noise ratio of the raw signal by canceling and/or removing the baseline signal, i.e., noise, from the raw signal to generate a desired signal that is indicative of substantially only the biological data.

Moreover, in the exemplary embodiment, computing device 200 may be selectively tuned to facilitate increasing the signal-to-noise ratio of the raw signal, the baseline signal, and/or the desired signal. For example, in the exemplary embodiment, computing device 200 is programmed to impedance match, i.e., tune, the raw signal, the baseline signal, and/or the desired signal based on biological data, environmental data, and/or other data. For example, in the exemplary embodiment, the raw signal, the baseline signal, and/or the desired signal may be tuned based on a type of clothing the occupant being monitored is wearing. That is, each clothing type and/or layer can have a respective tune circuit associated with it that enables a desired signal that is indicative of the biological data to be generated.

In the exemplary embodiment, computing device 200 determines a state of the occupant based on the desired signal or, more particularly, the biological data. More specifically, in the exemplary embodiment, computing device 200 creates a parameter matrix (not shown) that includes a plurality of footprints associated with the occupant's biological data over time. Generally, the plurality of footprints are indicative of the occupant in an operating state. However, when the biological data associated with at least one footprint deviates beyond a predetermined threshold from the biological data associated with the other footprints, computing device 200 may determine that the occupant is in a drowsy state. For example, in the exemplary embodiment, a heart rate and/or blood flow rate that is slower and/or is less than an average heart rate and/or blood flow rate by a predetermined amount may indicate drowsiness of the occupant.

In the exemplary embodiment, computing device 200 includes a memory device 210 and a processor 220 that is coupled to memory device 210 for executing programmed instructions. Processor 220 may include one or more processing units (e.g., in a multi-core configuration). In one embodiment, executable instructions and/or biological data are stored in memory device 210. For example, in the exemplary embodiment, memory device 210 stores software for use in converting a mechanical stress and/or vibration to a signal. Computing device 200 is programmable to perform one or more operations described herein by programming memory device 210 and/or processor 220. For example, processor 220 may be programmed by encoding an operation as one or more executable instructions and providing the executable instructions in memory device 210.

Processor 220 may include, but is not limited to, a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term processor.

Memory device 210, as described herein, is one or more devices that enable information such as executable instructions and/or other data to be stored and retrieved. Memory device 210 may include one or more computer readable media, such as, without limitation, dynamic random access memory (DRAM), static random access memory (SRAM), a solid state disk, and/or a hard disk. Memory device 210 may be configured to store, without limitation, executable instructions, biological data, and/or any other type of data suitable for use with the systems described herein.

In the exemplary embodiment, computing device 200 includes a presentation interface 230 that is coupled to processor 220. Presentation interface 230 outputs and/or displays information, such as, but not limited to, biological data and/or any other type of data to a user (not shown). For example, presentation interface 230 may include a display adapter (not shown) that is coupled to a display device (not shown), such as a cathode ray tube (CRT), a liquid crystal display (LCD), a light-emitting diode (LED) display, an organic LED (OLED) display, and/or an "electronic ink" display.

In the exemplary embodiment, computing device 200 includes an input interface 240 that receives input from a user. For example, input interface 240 receives instructions for controlling an operation of system 100 and/or any other type of data suitable for use with the systems described herein. In the exemplary embodiment, input interface 240 is coupled to processor 220 and may include, for example, a keyboard, a pointing device, a mouse, a stylus, a touch sensitive panel (e.g., a touch pad or a touch screen), a gyroscope, an accelerometer, a position detector, and/or an audio input interface. A single component, such as a touch screen, may function as both a display device of presentation interface 230 and as input interface 240.

In the exemplary embodiment, computing device 200 includes a communication interface 250 coupled to memory device 210 and/or processor 220. Communication interface 250 is coupled in communication with a remote device, such as first sensor 180, second sensor 190, and/or another computing device 200. For example, communication interface 250 may include, without limitation, a wired network adapter, a wireless network adapter, and/or a mobile telecommunications adapter.

In the exemplary embodiment, computing device 200 may be used to enable first sensor 180 to generate the alert signal. More specifically, in the exemplary embodiment, computing device 200 may be programmed to determine whether the alert signal is generated based on at least the raw signal from first sensor 180, the baseline signal from second sensor 190, and/or the desired signal generated by computing device 200. Moreover, in the exemplary embodiment, computing device 200 may be transmit a signal to first sensor 180 that enables first sensor 180 to transmit a tactile and/or audible signal that may be detected by the occupant. As such, in the exemplary embodiment, the occupant may be stimulated by the alert signal.

The subject matter described herein enables a state of an occupant to be determined. More specifically, the embodiments described herein facilitate increasing a signal indicative of an occupant's heart rate or blood flow rate and/or reducing undesired noise. Moreover, the embodiments described herein are generally more ergonomic and/or more comfortable relative to other known monitoring systems.

Exemplary embodiments of methods and systems for measuring a driver's heart rate and/or blood flow rate are described above in detail. The systems and methods are not limited to the specific embodiments described herein, but rather, components of systems and/or steps of the method may be utilized independently and separately from other components and/or steps described herein. Each component and each method step may also be used in combination with other components and/or method steps. Although specific features of various embodiments may be shown in some drawings and not in others, this is for convenience only. Any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A monitoring system that may be used to determine a state of an occupant of a vehicle, said monitoring system comprising:
   a seat comprising a seat back surface;
   a seat belt removably coupled to said seat, wherein said seat belt comprises a sash belt portion and a lap belt portion;
   a first sensor coupled to, the sash belt portion, said first sensor configured to generate a raw signal indicative of biological data and noise;
   a second sensor positioned remotely from said first sensor and coupled to the lap belt portion, said second sensor configured to generate a baseline signal indicative of noise associated with said first sensor; and
   a computing device that is programmed to determine the state of the occupant based on at least the raw signal and the baseline signal.

2. A monitoring system in accordance with claim 1, wherein said first sensor is fabricated from a flexible material.

3. A monitoring system in accordance with claim 1, said second sensor fabricated from a flexible material.

4. A monitoring system in accordance with claim 1, wherein said computing device is selectively tuned based on a tune circuit of at least one of biological data and environmental data, to increase a signal-to-noise ratio of the raw signal.

5. A monitoring system in accordance with claim 1, wherein said computing device is programmed to generate a desired signal based on at least the raw signal and the baseline signal, the desired signal indicative of the biological data.

6. A monitoring system in accordance with claim 1, wherein said first sensor is configured to generate an alert signal that is detectable by the occupant of the vehicle.

7. A monitoring system that may be used to determine a state of an occupant of a vehicle, said monitoring system comprising:
- a seat belt that comprises a sash belt portion and a lap belt portion;
- a first sensor coupled to said sash belt portion, said first sensor comprising a first piezoelectric film that is configured to generate a raw signal indicative of biological data and noise;
- a second sensor positioned remotely from said first sensor and coupled to the lap belt portion, said second sensor configured to generate a baseline signal indicative of noise associated with said first sensor; and
- a computing device that is programmed to determine the state of the occupant based on at least the raw signal and the baseline signal.

8. A monitoring system in accordance with claim 7, wherein said second sensor comprises a second piezoelectric film.

9. A monitoring system in accordance with claim 7, wherein said computing device is selectively tuned to increase a signal-to-noise ratio of the raw signal based on a tune circuit associated with at least one of biological data and environmental data.

10. A monitoring system in accordance with claim 7, wherein said computing device is programmed to generate a desired signal based on at least the raw signal and the baseline signal, the desired signal indicative of the biological data.

11. A monitoring system in accordance with claim 7, wherein said first sensor is configured to generate an alert signal that is detectable by the occupant of the vehicle.

12. A method of assembling a monitoring system that may be used to determine a state of an occupant of a vehicle, said method comprising:
- coupling a first sensor to a sash belt portion of a seat belt, the first sensor configured to generate a raw signal indicative of biological data and noise;
- positioning a second sensor remotely from the first sensor and coupling the second sensor to a lap belt portion of the seat belt, the second sensor configured to generate a baseline signal indicative of noise associated with the first sensor; and
- coupling the first sensor and the second sensor to a computing device that is programmed to determine the state of the occupant based on at least the raw signal and the baseline signal and is programmed to be selectively tunable to enable a signal-to-noise ratio of the raw signal to be increased based on a tune circuit associated with at least one of biological data and environmental data.

13. A method in accordance with claim 12, wherein coupling the first sensor coupling the second sensor allows the second sensor to detect noise that is substantially similar to noise associated with said first sensor.

14. A method in accordance with claim 12 further comprising programming the computing device to generate a desired signal based on at least the raw signal and the baseline signal, the desired signal indicative of the biological data.

15. A method in accordance with claim 12 further comprising programming the computing device to generate an alert signal based on the state of the occupant.

16. A system in accordance with claim 1 wherein said second sensor is positioned to detect noise that is substantially similar to noise detected by said first sensor.

\* \* \* \* \*